(12) United States Patent
Lee et al.

(10) Patent No.: US 11,974,955 B2
(45) Date of Patent: May 7, 2024

(54) FRAME MODULE AND MOTION ASSISTANCE APPARATUS INCLUDING THE SAME

(71) Applicants: SAMSUNG ELECTRONICS CO., LTD., Suwon-si (KR); Korea University of Technology and Education Industry-University Cooperation Foundation, Cheonan-si (KR)

(72) Inventors: Minhyung Lee, Anyang-si (KR); Jeonghun Kim, Hwaseong-si (KR); Se-Gon Roh, Suwon-si (KR); Youn Baek Lee, Yongin-si (KR); Jongwon Lee, Suwon-si (KR); Byungjune Choi, Gunpo-si (KR); Hyun Do Choi, Yongin-si (KR); Yong-Jae Kim, Cheonan-si (KR)

(73) Assignees: Samsung Electronics Co., Ltd., Suwon-si (KR); Korea University of Technology and Education Industry-University Cooperation Foundation, Cheonan-si (KR)

(*) Notice: Subject to any disclaimer, the term of this patent is extended or adjusted under 35 U.S.C. 154(b) by 221 days.

(21) Appl. No.: 17/542,628

(22) Filed: Dec. 6, 2021

(65) Prior Publication Data
US 2022/0087889 A1 Mar. 24, 2022

Related U.S. Application Data

(63) Continuation of application No. 15/014,607, filed on Feb. 3, 2016, now Pat. No. 11,191,691.

(30) Foreign Application Priority Data

Jul. 21, 2015 (KR) .................. 10-2015-0103129

(51) Int. Cl.
A61H 3/00 (2006.01)
A61F 2/60 (2006.01)
(Continued)

(52) U.S. Cl.
CPC ........... *A61H 1/0237* (2013.01); *A61F 2/604* (2013.01); *A61F 2/605* (2013.01); *A61F 2/70* (2013.01);
(Continued)

(58) Field of Classification Search
CPC ....................................... A61H 3/00
See application file for complete search history.

(56) References Cited

U.S. PATENT DOCUMENTS 7,416,538 B2 8/2008 Katoh et al.
7,780,616 B2 8/2010 Katoh et al.
(Continued)

FOREIGN PATENT DOCUMENTS

JP 2002-011027 A 1/2002
JP 2010-000205 A 1/2010
(Continued)

OTHER PUBLICATIONS

U.S. Appl. No. 15/014,607, filed Feb. 3, 2016; Lee et al.
(Continued)

*Primary Examiner* — Jacqueline Wozniki
(74) *Attorney, Agent, or Firm* — Nixon & Vanderhye P.C.

(57) ABSTRACT

A frame module includes a frame configured to enclose a portion of a user, and at least one reinforcement belt of which both end portions are connected to both sides of the frame, thereby restricting a splaying level of the frame in a predetermined direction.

20 Claims, 13 Drawing Sheets

(51) Int. Cl.
*A61F 2/70* (2006.01)
*A61H 1/02* (2006.01)

(52) U.S. Cl.
CPC ............. *A61H 1/0244* (2013.01); *A61H 3/00* (2013.01); *A61F 2002/608* (2013.01); *A61H 2003/007* (2013.01); *A61H 2201/163* (2013.01); *A61H 2201/1642* (2013.01); *A61H 2201/165* (2013.01); *A61H 2201/1652* (2013.01)

(56) References Cited

U.S. PATENT DOCUMENTS

| | | |
|---|---|---|
| 8,177,733 B2 | 5/2012 | Ashihara et al. |
| 8,545,424 B2 | 10/2013 | Hirata et al. |
| 8,652,075 B2 | 2/2014 | Takahashi et al. |
| 8,784,344 B2 | 7/2014 | Takahashi et al. |
| 9,022,956 B2 | 5/2015 | Kazerooni et al. |
| 2006/0276728 A1 | 12/2006 | Ashihara et al. |
| 2011/0160626 A1 | 6/2011 | Takahashi et al. |
| 2013/0253385 A1 | 9/2013 | Goffer et al. |
| 2014/0163435 A1 | 6/2014 | Yamamoto et al. |
| 2014/0296761 A1 | 10/2014 | Yamamoto et al. |

FOREIGN PATENT DOCUMENTS

| | | |
|---|---|---|
| JP | 5081740 B2 | 11/2012 |
| JP | 5163989 B2 | 3/2013 |

OTHER PUBLICATIONS

Korean Office Action dated Feb. 9, 2022 for KR Application No. 10-2015-01031128.
Korean Office Action dated Aug. 30, 2022 for KR Application No. 10-2015-0103129.

20

FRAME MODULE AND MOTION ASSISTANCE APPARATUS INCLUDING THE SAME

CROSS-REFERENCE TO RELATED APPLICATION

This application is a continuation of U.S. Ser. No. 15/014,607, filed Feb. 3, 2016, and which claims the priority benefit of Korean Patent Application No. 10-2015-0103129, filed on Jul. 21, 2015, in the Korean Intellectual Property Office, the entire contents of which are incorporated herein by reference in its entirety.

BACKGROUND

1. Field

At least one example embodiment relates to a frame module and/or a motion assistance apparatus including the same.

2. Description of the Related Art

With the onset of rapidly aging societies, there may be an increase in the number of people experiencing inconvenience and/or pain from joint problems. Thus, there is a growing interest in motion assistance apparatuses enabling the elderly and/or patients having joint problems to walk with less effort. Furthermore, motion assistance apparatuses increasing muscular strength of human bodies are desired for military purposes.

In general, motion assistance apparatuses for assisting motion of lower parts of bodies may include body frames disposed on trunks of users, pelvic frames coupled to lower sides of the body frames to cover pelvises of the users, femoral frames disposed on thighs of the users, sural frames disposed on calves of the users, and/or pedal frames disposed on feet of the users. The pelvic frames and femoral frames may be connected rotatably by hip joint portions, the femoral frames and sural frames may be connected rotatably by knee joint portions, and/or the sural frames and pedial frames may be connected rotatably by ankle joint portions.

SUMMARY

Some example embodiments relate to a frame module.

In some example embodiment, the frame module may include a frame configured to enclose a portion of a user, and at least one reinforcement belt of which both end portions are connected to both sides of the frame, thereby restricting a splaying level of the frame in a predetermined direction.

A length of the reinforcement belt may be adjustable.

The reinforcement belt may include a first sub-belt of which one end portion is connected to one side of the frame, and a second sub-belt of which one end portion is connected to another side of the frame. Another end portion of the first sub-belt may be detachable from another end portion of the second sub-belt.

One end portion of at least one of the first sub-belt and the second sub-belt may be rotatably connected to the frame.

The both end portions of the reinforcement belt may be connected to inner surfaces of the frame to support the user in a state in which the user is spaced apart from the frame.

At least one of the both end portions of the reinforcement belt may be rotatably connected to the frame.

A plurality of reinforcement belts may be provided, and the plurality of reinforcement belts may be connected to a single hinge axis provided in the frame.

A plurality of reinforcement belts may be provided, and the plurality of reinforcement belts may be connected to each other to form a single closed loop.

The frame may include a joint mounting portion in which a rotating member configured to be rotated by a driving module is to be installed, and the reinforcement belt may correspond to a joint belt of which one end portion is connected to one side of the joint mounting portion.

The frame may include a supporting member configured to extend in a direction perpendicular to a circumferential direction of the portion of the user to support a body of the user, and the reinforcement belt may correspond to a supporting belt of which one end portion is connected to an end portion of the supporting member.

The frame may include an upper supporting member and a lower supporting member configured to extend upward and downward in a direction perpendicular to a circumferential direction of the portion of the user, and the frame module may further include an upper supporting belt of which one end portion is connected to the upper supporting member, and a lower supporting belt of which one end portion is connected to the lower supporting member.

The reinforcement belt may correspond to a crossing belt connected to the frame in a direction intersecting a circumferential direction of the portion of the user.

The reinforcement belt may correspond to a parallel belt connected to the frame in a direction parallel to a circumferential direction of the portion of the user.

The frame may include a joint mounting portion in which a rotating member configured to be rotated by a driving module is to be disposed, and a supporting member configured to extend in a direction perpendicular to a circumferential direction of the portion of the user to support a body of the user, and both end portions of the parallel belt may be connected to one side of the joint mounting portion and one side of the supporting member.

The reinforcement belt may correspond to a bone belt disposed in a longitudinal direction of a bone of the user.

The bone belt may correspond to an iliac crest belt disposed along an iliac crest of the user.

The frame may include a joint mounting portion in which a rotating member configured to be rotated by a driving module is to be disposed. One side of the iliac crest belt may be connected to one side of the joint mounting portion, and another side of the iliac crest belt may be connected to a front portion of the frame.

The frame may include an upper supporting member and a lower supporting member configured to extend upward and downward in a direction perpendicular to a circumferential direction of the portion of the user, and the reinforcement belt may correspond to a connecting belt configured to connect an end portion of the upper supporting member to an end portion of the lower supporting member.

The frame may include a supporting member configured to extend in a direction perpendicular to a circumferential direction of the portion of the user to support a body of the user, and the reinforcement belt may correspond to a side belt of which one side is connected to the supporting member and another side is connected to a front portion of the frame.

Other example embodiments relate to a motion assistance apparatus.

In some example embodiments, the motion assistance apparatus may include a driving module configured to generate power to assist a motion of a user, a rotating member configured to be rotated by the driving module to assist a rotary motion of a joint portion of the user, and a frame module including a frame configured to enclose a portion of the user, the frame including a joint mounting portion in which the rotating member is to be disposed, and at least one reinforcement belt connected to both sides of the frame to reinforce a stiffness of the frame.

The frame may further include a supporting member configured to extend in a direction perpendicular to a circumferential direction of the portion of the user to support a body of the user, and the reinforcement belt may include a joint belt of which one end portion is connected to one side of the joint mounting portion, and a supporting belt of which one end portion is connected to an end portion of the supporting member.

Some example embodiments relate to a frame module.

In some example embodiments, the frame module includes a plurality of interlocking frames configured to enclose a portion of a user; and at least one reinforcement belt configured to restrict a deformation of the plurality of interlocking frames in response to a torque applied thereto.

In some example embodiments, the plurality of interlocking frames are flexible frames and are separated by an adjustable distance to secure the frame module onto the portion of the user, the plurality of interlocking frames configured to have joint assemblies mounted thereon, the joint assemblies configured to apply a torque to a support attached to at least a thigh of the user to assist the user with movement of their hip joints.

In some example embodiments, the plurality of interlocking frames includes a first interlocking frame and a second interlocking frame, and the at least one reinforcement belt includes a first sub-belt and a second sub-belt connected to the first interlocking frame and the second interlocking frame, respectively, the first sub-belt configured to detach from the second sub-belt to allow the user to remove the frame module.

In some example embodiments, the at least one reinforcement belt includes a plurality of reinforcement belts connected together in a closed loop.

In some example embodiments, the ends of each of the plurality of reinforcement belts are connected to inner surfaces of the plurality of interlocking frames such that the at least one reinforcement belt is configured to maintain a gap between the plurality of interlocking frames and the user when the torque is applied to the plurality of interlocking frames.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
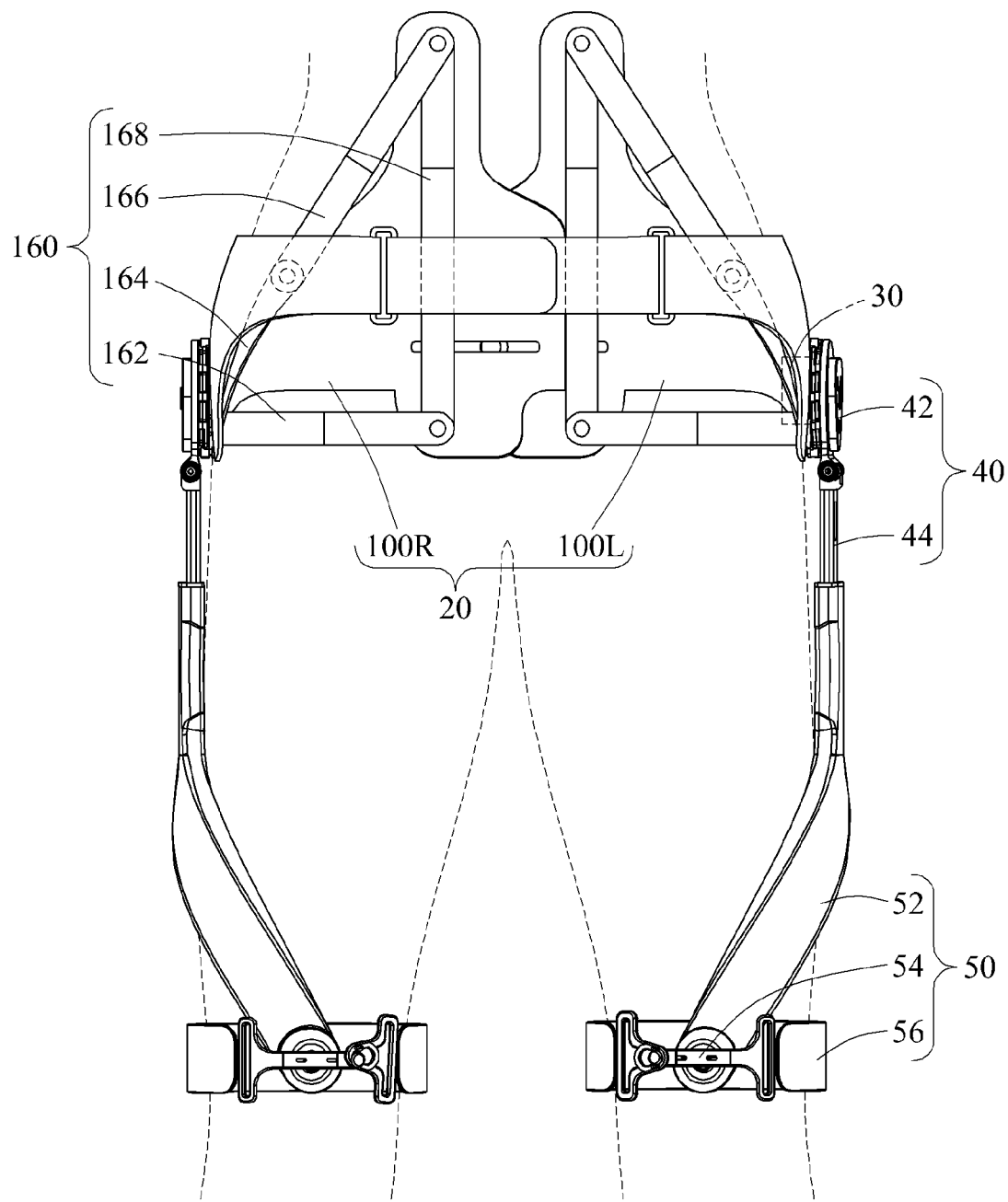
FIG. 1 is a front view of a motion assistance apparatus according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Figure 2:
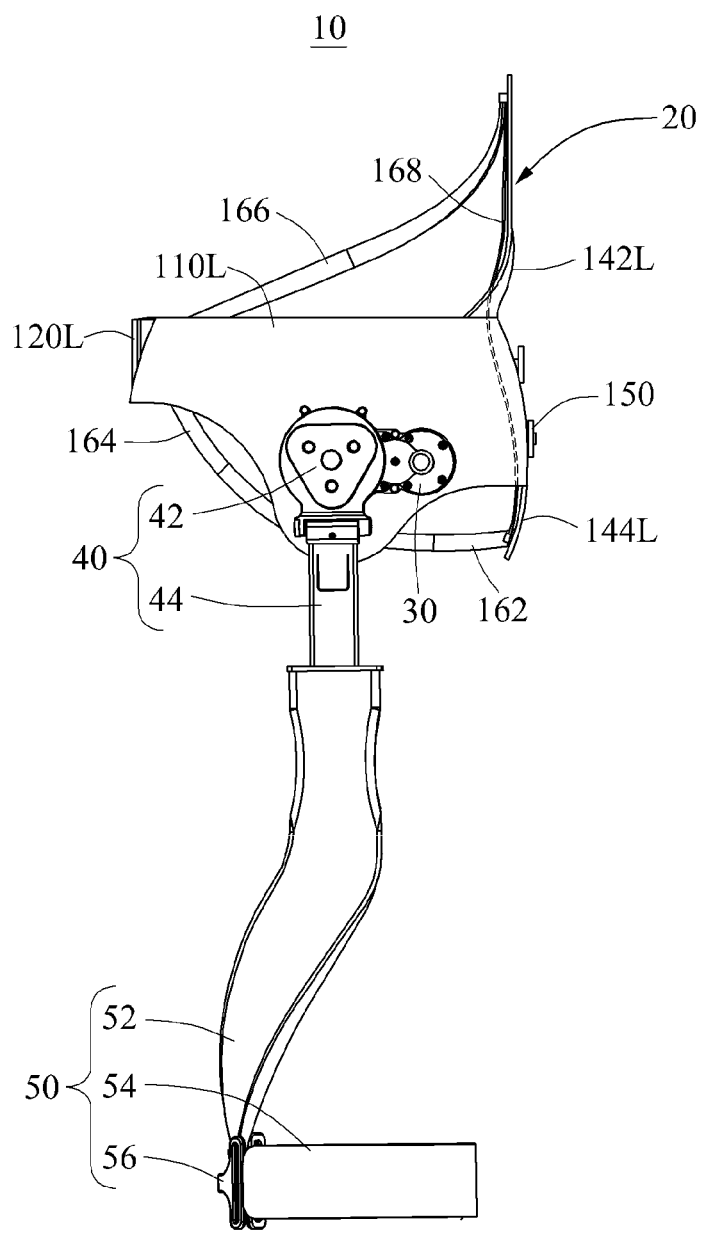
FIG. 2 is a side view of a motion assistance apparatus according to at least one example embodiment.

FIG. 1 is a front view of a motion assistance apparatus according to at least one example embodiment, and FIG. 2 is a side view of a motion assistance apparatus according to at least one example embodiment.

Referring to FIGS. 1 and 2, a motion assistance apparatus 10 may be worn by a user to assist a motion of the user.

The user may correspond to a human, an animal, or a robot. However, the user is not limited thereto. In addition, although FIG. 1 illustrates a case in which the motion assistance apparatus 10 assists the thighs of the user, the motion assistance apparatus 10 may also assist a motion of an upper body, for example, a hand, an upper arm, and a lower arm of the user. Further, the motion assistance apparatus 10 may assist a motion of another part of a lower body, for example, a foot, and a calf of the user. The motion assistance apparatus 10 may assist a motion of a part of the user.

Hereinafter, a case in which the motion assistance apparatus 10 assists motions of thighs of a human will be described. However, example embodiments are not limited thereto.

The motion assistance apparatus 10 may include a frame module 20, a driving module 30, a joint assembly 40, and a supporting module 50.

The frame module 20 may be fixed to the user. The frame module 20 may be provided in a form of covering an outer surface of the user. For example, the frame module 20 may be fixed to a side of a waist of the user, and include a curved surface corresponding to a contact portion of the user. The frame module 20 includes a first side frame 100L disposed on one side of the waist of the user, a second side frame 100R disposed on another side of the waist of the user, and a reinforcement belt 160. The first side frame 100L and the second side frame 100R may be detachable from each other, or provided as an integral body. The first side frame 100L and the second side frame 100R may be referred to as interlocking frames.

The frame module 20 may have flexibility to be in close contact with a body of the user. For example, the frame module 20 may be formed using a flexible material, or may be formed using a rigid material in a sufficiently thin thickness. In this example, the frame module 20 may also be referred to as a flexible frame module.

When the frame module 20 has flexibility as described above, the frame module 20 may be bent by a force or torque generated by the driving module 30. In particular, to assist a walking motion of the user, respective driving modules 30 disposed on both sides of the frame module 20 may rotate in opposite directions. In this example, torques in different directions may be alternately applied to the both sides of the frame module 20, whereby the frame module 20 may be distorted in response to the motions of the driving modules 30. Accordingly, the frame module 20 may further include at least one reinforcement belt 162, 164, 166, and 168 to prevent the distortion of the frame module 20. The at least one reinforcement belt 162, 164, 166, and 168 may be collectively referred to as the reinforcement belt 160.

The reinforcement belt 160 may be provided in at least one of the first side frame 100L and the second side frame 100R. In some example embodiments, the reinforcement belt 160 may correspond to a fabric material with little elasticity such that the reinforcement belt 160 may be relatively thin as compared to a thick, heavy reinforcing agent. Thus, a sufficient stiffness may be secured without increasing the total weight of the frame module 20. Each side of the reinforcement belt 160 may be fixed to a portion of the at least one side frame, thereby reinforcing the stiffness of the frame module 20 in a required direction. The reinforcement belt 160 may prevent splaying of the frame module 20 in an undesired direction.

The reinforcement belt 160 may be provided in an inner surface of the at least one side frame 100R, 100L. In such a state, by adjusting a length of the reinforcement belt 160 to be sufficiently short, the reinforcement belt 160 may support the user in a state in which the user is spaced apart from the inner surface of the at least one side frame 100R, 100L. In this example, the reinforcement belt 160 may prevent a direct contact between the body of the user and the at least one side frame 100R, 100L, thereby increasing wearability and breathability.

At least one of the end portions of the reinforcement belt 160 may be rotatably connected to the at least one side frame 100R, 100L. For example, a connection angle between the reinforcement belt 160 and the at least one side frame may be changeable. In this example, the reinforcement belt 160 may rotate to be suitable for a shape of the body of the user, thereby increasing wearability for the user.

The driving module 30 may provide power to be transmitted to the joint assembly 40. For example, the driving module 30 may be disposed in a lateral direction of the joint assembly 40 such that an axis of rotation of the diving module 30 may be spaced apart from an axis of rotation of the joint assembly 40. Therefore, when compared to a case in which the driving module 30 and the joint assembly 40 share an axis of rotation, a protruding height from the user may relatively decrease. In other example embodiments, the driving module 30 may be more spaced apart from the joint assembly 40. Therefore, a power transmitting module may be additionally provided to transmit power from the driving module 30 to the joint assembly 40. The power transmitting module may be a rotary body such as, for example, a gear, or a longitudinal member such as, for example, a wire, a cable, a string, a rubber band, a spring, a belt, and a chain.

The joint assembly 40 may receive power from the driving module 30, and assist a motion of a joint portion of the user. The joint assembly 40 may be disposed on one or more of the sides of the frame module 20 at a position corresponding to the joint portion of the user. One end of the joint assembly 40 may be connected to the driving module 30, and another end of the joint assembly 40 may be connected to the supporting module 50.

The joint assembly 40 may include a rotating member 42, and a connecting member 44. The rotating member 42 may rotate using power received from the driving module 30. For example, the rotating member 42 may be disposed on one or more of the sides of the hip joints of the user. The connecting member 44 may connect the rotating member 42 to the supporting module 50, and rotate using torque of the rotating member 42. The connecting member 44 may be provided, for example, in a hinge connection structure. By a hinge axis of the hinge connection structure and an axis of rotation of the rotating member 42, the supporting module 50 may perform a two degree of freedom (DOF) motion with respect to the frame module 20.

The supporting module 50 may support a portion of the user, and assist a motion of the portion of the user. The supporting module 50 may be configured to rotate using torque of the joint assembly 40. The supporting module 50 may include a supporting frame 52, an applying member 54, and a supporting band 56.

The supporting frame 52 may transmit force to a portion of the user. One end portion of the supporting frame 52 may be rotatably connected to the joint assembly 40, and another end portion of the supporting frame 52 may be connected to the supporting band 56 to transmit force to a portion of the user. For example, the supporting frame 52 may push or pull a thigh of the user. The supporting frame 52 may extend and be bent in a longitudinal direction of the thigh of the user to cover at least a portion of the circumference of the thigh of the user. The one end portion of the supporting frame 52 may be disposed on a side surface of the thigh of the user, and the other portion of the supporting frame 52 may be disposed on a front surface of the thigh of the user. A surface on the side of the one end portion of the supporting frame 52 may be orthogonal to a surface on the side of the other end portion of the supporting frame 52.

The supporting frame 52 may be movably connected to the connecting member 44. By relative motions of the supporting frame 52 and the connecting member 44, a total length from the joint assembly 40 to the supporting band 56 may be variable. In this example, the supporting module 50 may perform a three DOF motion with respect to the frame module 20.

The applying member 54 may be connected to the other end portion of the supporting frame 52 to apply force to a portion of the user. For example, the applying member 54 may be disposed along the front surface of the thigh of the user, or in a circumferential direction of the thigh of the user to push or pull the thigh of the user. The applying member 54 may include a curved surface corresponding to the thigh of the user, and configured to extend from the other end portion of the supporting frame 52 toward both sides of the supporting frame 52.

The supporting band 56 may be connected to one side of the applying member 54. For example, the supporting band 56 may be disposed to cover a circumference of at least a portion of the thigh of the user, thereby preventing separation between the thigh of the user and the supporting frame 52.

Meanwhile, the driving module and/or the supporting module may be additionally provided. For example, the supporting module 50 may extend to a knee, and an additional joint assembly may be provided in the supporting module 50 at a position corresponding to a knee joint. Further, an additional supporting module may be connected to the additional joint assembly. The additional supporting module may support a calf of the user, thereby assisting a motion of the calf. Here, an actuator configured to drive the additional joint assembly may be disposed on one side of the additional joint assembly, or may be disposed in, for example, the frame module 20, to be spaced apart from the additional joint assembly.

Figure 3:
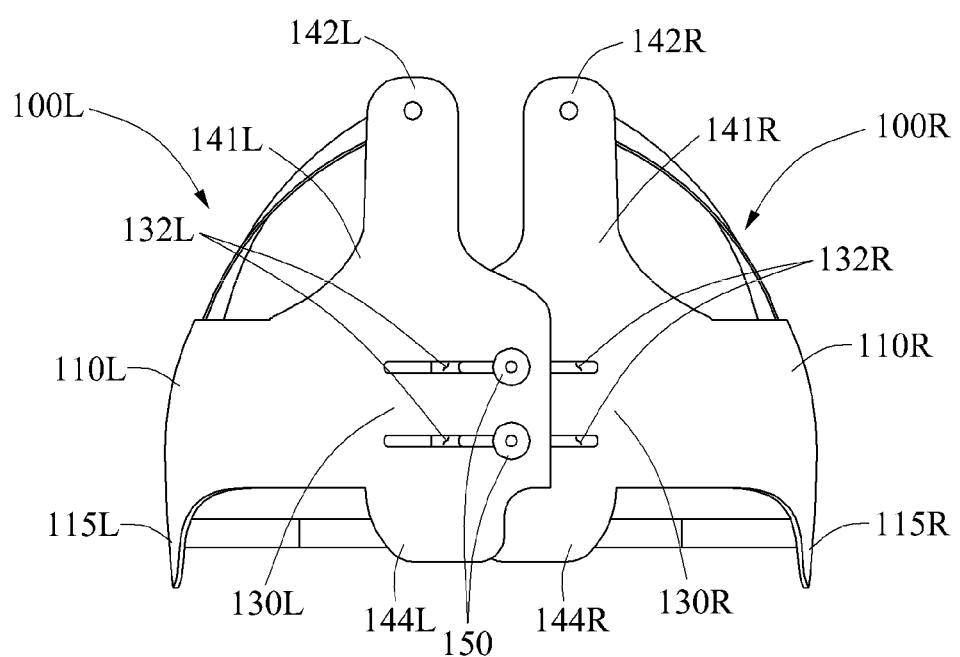
FIG. 3 is a rear view of a frame module according to at least one example embodiment.
Figure 4:
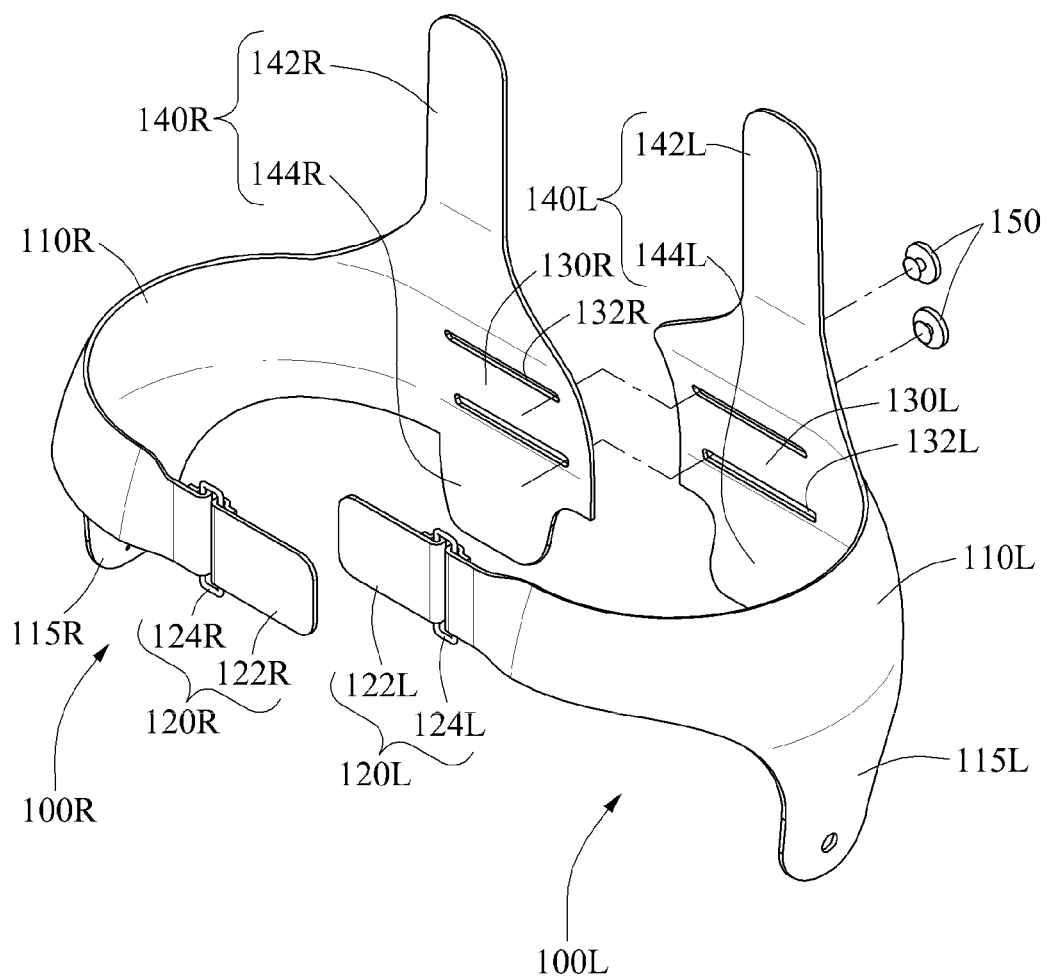
FIG. 4 is an exploded perspective view of a frame module according to at least one example embodiment.

FIG. 3 is a rear view illustrating a frame module according to at least one example embodiment, and FIG. 4 is an exploded perspective view illustrating a frame module according to at least one example embodiment. For ease of description, a reinforcement belt is omitted in FIG. 4.

Referring to FIGS. 3 and 4, the frame module 20 may include the first side frame 100L, the second side frame 100R, and a fastening member 150. The first side frame 100L and the second side frame 100R may be connected to each other to form a single closed curve. The first side frame 100L and the second side frame 100R may be detachable from each other. Therefore, the first side frame 100 and the second side frame 100R may also be referred to as a "first separable frame" and a "second separable frame", respectively. In the structure as illustrated in FIGS. 3 and 4, by adjusting a fastening distance of the first side frame 100L and the second side frame 100R based on a body shape of the user, wearability for the user may increase.

The first side frame 100L may cover one side surface of the waist of the user, a portion of a front surface of the waist of the user, and a portion of a rear surface of the waist of the user. The first side frame 100L may be provided roughly in a U-shape. The first side frame 100L may be provided using a relatively thin board. The first side frame 100L may be provided using a flexible material to improve a degree of contact with the user. In this example, the first side frame 100L may be deformed based on a shape of the user to be in close contact with the user. The first side frame 100L may include a first central portion 110L, a first front extending portion 120L, and a first rear extending portion 130L.

The first central portion 110L may include a curved surface corresponding to one side surface of the user, and be disposed on the one side surface of the user. The first central portion 110L may include a joint mounting portion 115L configured to extend toward a hip joint portion of the user. The joint mounting portion 115L may be provided to cover the hip joint portion. The rotating member 42 of FIG. 1 may be provided on the joint mounting portion 115L.

The first front extending portion 120L may extend from the first central portion 110L to cover at least a portion of the front surface of the user. The first front extending portion 120L may be detachable from the second side frame 100R. For example, the first front extending portion 120L may include a first binding portion 122L, and a first connecting portion 124L.

The first binding portion 122L may be detachable from the second side frame 100R. For example, the first binding portion 122L may include a base plate having a shape of a board, and a hook and loop fastener provided on the base plate. In other example embodiments, the first binding portion 122L may also be fastened with the second side frame 100R in a structure of a buckle. However, the shape of the first binding portion 122L is not limited thereto.

The first connecting portion 124L may rotatably connect the first binding portion 122L to the first central portion 110L. For example, the first connecting portion 124L may be a ring or a hinge.

The first rear extending portion 130L may extend from the first central portion 110L to cover at least a portion of the rear surface of the user. The first rear extending portion 130L may extend from the first central portion 110L toward an opposite side of the first front extending portion 110L. The first rear extending portion 130L may be disposed on the opposite side of the first front extending portion 120L based on the user. The first rear extending portion 130L may be detachable from the second side frame 100R.

The first rear extending portion 130L includes a first guide portion 132L. The first guide portion 132L may guide the second side frame 100R to slide with respect to the first rear extending portion 130L. The first guide portion 132L may be a slot provided lengthwise in an extending direction of the first rear extending portion 130L. In this example, the first guide portion 132L may also be referred to as a "guide slot". A plurality of first guide portions 132L may be provided. The plurality of first guide portions 132L may be provided in parallel. The fastening member 150 may be connected to the first guide portion 132L.

The first side frame 100L may further include a first supporting member 140L. The first supporting member 140L may include a first upper supporting member 142L and a first lower supporting member 144L.

The first upper supporting member 142L may extend from the first rear extending portion 130L in an upward direction to support an upper side of the user. The first upper supporting member 142L may extend in a direction orthogonal to a longitudinal direction of the first rear extending portion 130L. For example, the first upper supporting member 142L may support a dorsal portion of the user. The first upper supporting member 142L may extend from the first rear extending portion 130L to a portion corresponding to about a midpoint of the dorsal portion of the user. The first upper supporting member 142L may include a first extension 141L whose width increases in a direction of the first rear extending portion 130L.

The first upper supporting member 142L may efficiently prevent a rotation of the first side frame 100L by the torque generated by the driving module 30. For example, referring to FIG. 4, when the driving module 30 rotates counterclockwise, counterclockwise torque may be applied to the first side frame 100L. In this example, the first upper supporting member 142L having a long moment arm from the driving module 30 may prevent a counterclockwise rotation of the first side frame 100L by reaction force received from the back of the user, while transferring relatively small force to the back of the user.

The first lower supporting member 144L may extend from the first rear extending portion 130L in a downward direction to support a lower side of the user. The first lower supporting member 144L may extend in a direction orthogonal to the longitudinal direction of the first rear extending portion 130L. For example, the first lower supporting member 144L may support a hip portion of the user.

The first lower supporting member 144L may efficiently prevent a rotation of the first side frame 100L by the torque generated by the driving module 30. For example, referring to FIG. 4, when the driving module 30 rotates clockwise, clockwise torque may be applied to the first side frame 100L. In this example, the first lower supporting member 144L having a long moment arm from the driving module 30 may prevent a clockwise rotation of the first side frame 100L by reaction force received from a hip of the user, while transferring relatively small force to the hip of the user.

The second side frame 100R may be provided in a shape symmetrical to the first side frame 100L. Hereinafter, the same names may be used to describe the elements included in the first side frame 100L described above and elements having common functions. Unless otherwise mentioned, the descriptions related to the first side frame 100L may be applicable to the second side frame 100R.

The second side frame 100R may cover a remaining portion of the waist of the user yet to be covered by the first side frame 100L. The second side frame 100R may cover another side of the waist of the user, a remaining portion of the front surface of the waist of the user, and a remaining portion of the rear surface of the waist of the user. At least a portion of the second side frame 100R may overlap the first side frame 100L. The second side frame 100R may include a second central portion 110R, a second front extending portion 120R, and a second rear extending portion 130R.

The second central portion 110R may include a curved surface corresponding to another side surface of the user, and be disposed on the other side surface of the user. The second central portion 110R may be disposed to face the first central portion 110L. The second central portion 110R may include a joint mounting portion 115R configured to extend toward a hip joint portion of the user. The joint mounting portion 115R may be provided to cover the hip joint portion.

The second front extending portion 120R may extend from the second central portion 110R to cover at least a portion of the front surface of the user. The second front extending portion 120R may be detachable from the first binding portion 122L. For example, the second front extending portion 120R may include a second binding portion 122R, and a second connecting portion 124R.

The second binding portion 122R may be detachable from the first binding portion 122L. For example, the second binding portion 122R may include a hook and loop fastener corresponding to the first binding portion 122L. In other example embodiments, the second binding portion 122R may include a structure of a buckle corresponding to the first binding portion 122L.

The second connecting portion 124R may rotatably connect the second binding portion 122R to the second central portion 110R.

The second rear extending portion 130R may extend from the second central portion 110R to cover at least a portion of the rear surface of the user. The second rear extending portion 130R may extend from the second central portion 110R towards an opposite side of the second front extending portion 120R. The second rear extending portion 130R may be disposed on the opposite side of the second front extending portion 120R based on the user. The second rear extending portion 130R may be detachable from the first rear extending portion 130L.

The second rear extending portion 130R may include a second guide portion 132R. The second guide portion 132R may guide the first rear extending portion 130L to slide with respect to the second rear extending portion 130R. The second guide portion 132R may be a slot provided lengthwise in an extending direction of the second rear extending portion 130R. The second guide portion 132R may be provided in a shape corresponding to the first guide portion 132L. When the second rear extending portion 130R overlaps the first rear extending portion 130L, the second guide portion 132R may overlap at least a portion of the first guide portion 132L. The fastening member 150 may be connected to the overlapping portion between the second guide portion 132R and the first guide portion 132L. The fastening member 150 may fasten the second rear extending portion 130R with the first rear extending portion 130L.

The second side frame 100R may further include a second supporting member 140R. The second supporting member 140R may include a second upper supporting member 142R, and a second lower supporting member 144R.

The second upper supporting member 142R may be provided in a shape symmetrical to the first upper supporting member 142L. The second upper supporting member 142R and the first upper supporting member 142L may be disposed on both sides based on a spine of the user, to support erector spinae muscles of the user.

The second lower supporting member 144R may be provided in a shape symmetrical to the first lower supporting member 144L. The second lower supporting member 144R and the first lower supporting member 144L may be disposed to support hip muscles of the user.

The fastening member 150 may fasten the first side frame 100L with the second side frame 100R. The fastening member 150 may penetrate through the first guide portion 132L and the second guide portion 132R to prevent relative movements of the first rear extending portion 130L and the second rear extending portion 130R. In an example, the fastening member 150 may include a bolt and a nut configured to pressurize the first rear extending portion 130L and the second rear extending portion 130R simultaneously. In another example, one of the first guide portion 132L and the second guide portion 132R may be provided in a form of a threaded hole, and the fastening member 150 may be a bolt having threads corresponding to the hole.

Figure 5:
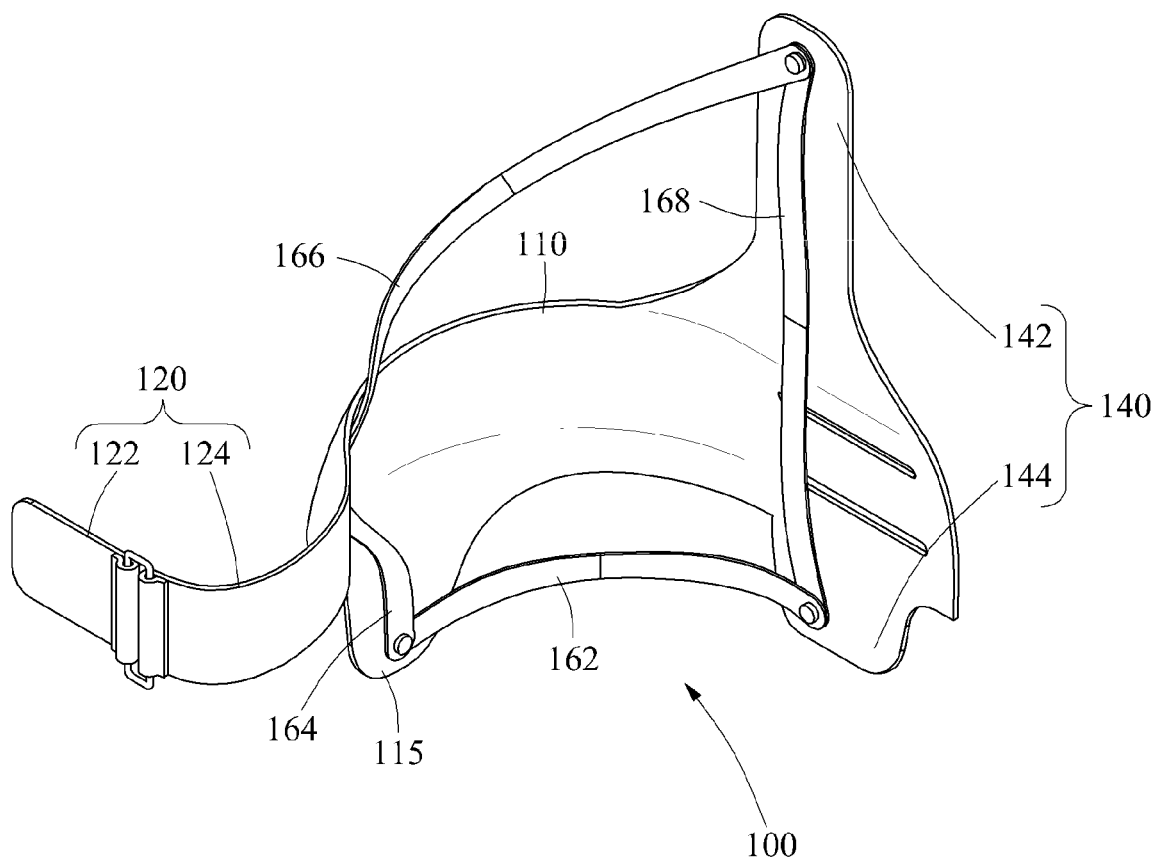
FIG. 5 is a view illustrating an installation structure of a reinforcement belt according to at least one example embodiment.

FIG. 5 is a view illustrating an installation structure of a reinforcement belt according to at least one example embodiment.

Referring to FIG. 5, both end portions of the reinforcement belt 160 may be fixed to both portions of a side frame 100 to restrict an elongating level of the side frame 100 in a desired (or, alternatively, a predetermined) direction. For example, the reinforcement belt 160 may restrict a maximum elongation distance of the side frame 100. In further detail, the reinforcement belt 160 may reinforce a strength of the side frame 100, thereby preventing splaying (or, alternatively, stretching or deformation) of the side frame 100. The reinforcement belt 160 may be disposed to be in close contact with the user, and distribute force or torque applied to the side frame 100 by the driving module 30 to the body of the user. Accordingly, the reinforcement belt 160 may prevent an impact to the user caused in response to a serious distortion of a portion of the side frame 100 positioned at a relatively long distance from the driving module 30. Further, the reinforcement belt 160 may prevent an excessive distortion of the side frame 100, thereby increasing wearability for the user. In addition, the reinforcement belt 160 may reduce an error or uncertainty caused in response to the distortion of the side frame 100, thereby helping to control assistance force precisely.

The frame module 20 may include joint belts 162 and 164. One end portion of each of the joint belts 162 and 164 may be connected to one side of a joint mounting portion 115. The joint belts 162 and 164 may reduce force or torque transferred to the joint mounting portion 115. The joint mounting portion 115 may correspond to a portion in which the force or torque generated by the driving module 30 is transferred directly to the frame module 20. Thus, the joint mounting portion 115 may reduce bending of a portion of the frame module 20 disposed on a path along which the force or torque is propagated from the joint mounting portion 115 to another portion of the frame module 20.

The frame module 20 may include an upper supporting belt 166 of which one end portion is connected to an upper supporting member 142, and a lower supporting belt 168 of which one end portion is connected to a lower supporting member 144. For example, another end portion of the upper supporting belt 166 may be connected to a front portion of the side frame 100, and another end portion of the lower supporting belt 168 may be connected to the joint mounting portion 115. The upper supporting belt 166 and the lower supporting belt 168 may be collectively referred to as supporting belts 166 and 168. The upper supporting member 142 or the lower supporting member 144 may have a relatively long moment arm from the driving module 30, compared to other portions of the frame module 20. Thus, the supporting belts 166 and 168 may reduce splaying (or, alternatively, stretching or deformation) of the frame module 20 while transferring relatively small force to the body of the user.

The joint belt 164, the upper supporting belt 166, and the lower support belt 168 of the frame module 20 may be considered crossing belts 164, 166, and 168 connected in a direction intersecting a circumferential direction of the waist of the user. The crossing belts 164, 166, and 168 may prevent splaying (or, alternatively, stretching or deformation) of the frame module 20 due to torque generated by the driving module 30 in a direction of the torque. Further, the crossing belts 164, 166, and 168 may prevent bobbing of the frame module 20, in detail, an occurrence of a pitch rotation motion, rather than being in close contact with the user.

The joint belt 162 of the frame module 20 may be considered a parallel belt 162 that is parallel to a circumferential direction of the waist of the user. The parallel belt 162 may prevent splaying (or, alternatively, stretching or deformation) of the frame module 20 in the circumferential direction of the waist, thereby preventing a reduction in a degree of contact in response to the distortion of the frame module 20. For example, both end portions of the parallel belt 162 may be connected to one side of the joint mounting portion 115 and one side of the lower supporting member 144.

The joint belt 164 of the frame module 20 may be considered a bone belt 164 disposed in a longitudinal direction of a bone of the user. For example, the bone belt 164 may be disposed along an iliac crest of a human. In this example, the bone belt 164 may also be referred to as an iliac crest belt. The iliac crest is a bone protruding around a pelvis outward relatively much. A skin layer around the iliac crest is relatively thin, compared to other portions, and thus, the iliac crest may be a suitable supporter. One side of the iliac crest belt may be connected to one side of the joint mounting portion 115, and another side of the iliac crest belt may be connected to a front portion of the side frame 100, for example, a central portion 110 or a front extending portion 120.

The lower support belt 168 of the frame module 20 may be considered a connecting belt 168 configured to connect an end portion of the upper supporting member 142 to an end portion of the lower supporting member 144. The upper supporting member 142 and lower supporting member 144 may have long moment arms from the driving module 30 in upward and downward directions, respectively. Accordingly, the upper supporting member 142 and lower supporting member 144 may reduce an effect of the driving module 30 using relatively small force. The connecting belt 168 may reinforce the stiffness of end portions of the upper supporting member 142 and the lower supporting member 144, thereby increasing the aforementioned functions of the upper supporting member 142 and the lower supporting member 144.

The upper support belt 166 of the frame module 20 may be considered a side belt 166 of which one side is connected to the upper supporting member 142 or the lower supporting member 144 and another side is connected to a front portion of the side frame 100, for example, the central portion 110 or the front extending portion 120. Although the connecting belt 168 may not prevent a distortion occurring when the upper supporting member 142 and the lower supporting member 144 rotate in the same direction, the side belt 166 may prevent such a distortion. For example, one side of the side belt 166 may be connected to the upper supporting member 142, and another side of the side belt 166 may extend to the central portion 110.

At least two of the plurality of belts 162, 164, 166, and 168 may be connected to each other. For example, the at least two belts may be rotatably connected to a single hinge provided in the frame module 20. When force or torque that splays the frame module 20 is applied to one of the belts connected to each other, the force or torque may be distributed and transferred to a remaining belt, whereby wearability for the user may increase. The frame module 20 may include a plurality of belts 162, 164, 166, and 168 that form a single closed loop.

The aforementioned joint belts, supporting belts, crossing belts, parallel belt, bone belt, connecting belt, and side belt may be collectively referred to as the reinforcement belt 160. Meanwhile, depending on a fastening position of the reinforcement belt 160, a single reinforcement belt 160 may perform functions of at least two of the seven types of reinforcement belts as described above. Further, in some example embodiments, one or more of the seven types of reinforcement belts described above may be omitted. For example, in some example embodiments one or more of belts 162, 164, 166 and 168 may be omitted.

Figure 6:
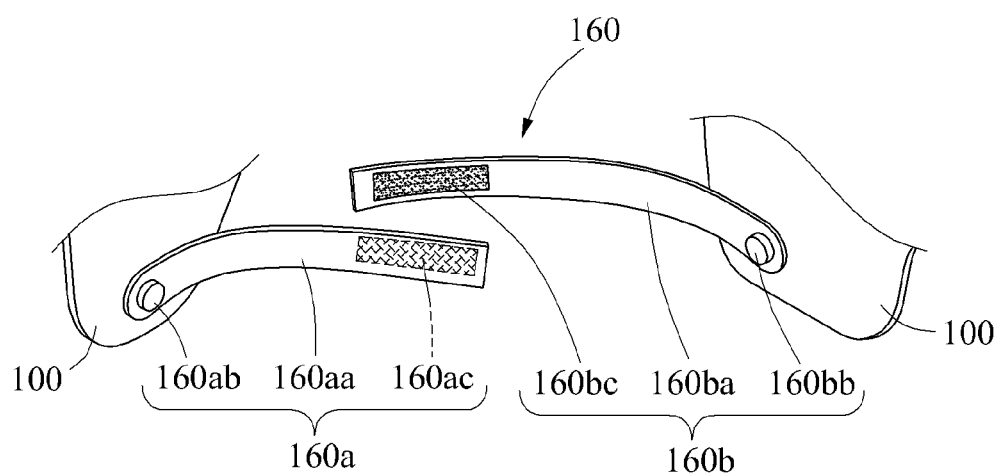
FIG. 6 is a view illustrating a reinforcement belt according to at least one example embodiment.

FIG. 6 is a view illustrating a reinforcement belt according to at least one example embodiment.

Referring to FIG. 6, a length of the reinforcement belt 160 may be adjustable. A user may adjust the length of the reinforcement belt 160 so that the reinforcement belt 160 may be in close contact with a body of the user. The reinforcement belt 160 may include a first sub-belt 160*a* and a second sub-belt 160*b* that may be separate from or fastened to each other.

The first sub-belt 160*a* may include a sub-belt body 160*aa*, a frame connecting portion 160*ab* connected to the side frame 100, and a sub-belt connecting portion 160*ac* connected to the second sub-belt 160*b*.

The frame connecting portion 160*ab* may be rotatably connected to, for example, the side frame 100. In some example embodiments, the frame connecting portion 160*ab* may have a structure of a hinge.

The sub-belt connecting portion 160*ac* may be detachable from, for example, the second sub-belt 160*b*. For example, the sub-belt connecting portion 160*ac* may have a structure of a hook and loop fastener.

The second sub-belt 160*b* may include, similar to the first sub-belt 160*a*, a sub-belt body 160*ba*, a frame connecting portion 160*b* b, and a sub-belt connecting portion 160*bc*.

In the structure as described above, the length of the reinforcement belt 160 may be adjusted to be suitable for a body shape of the user.

Figure 7:
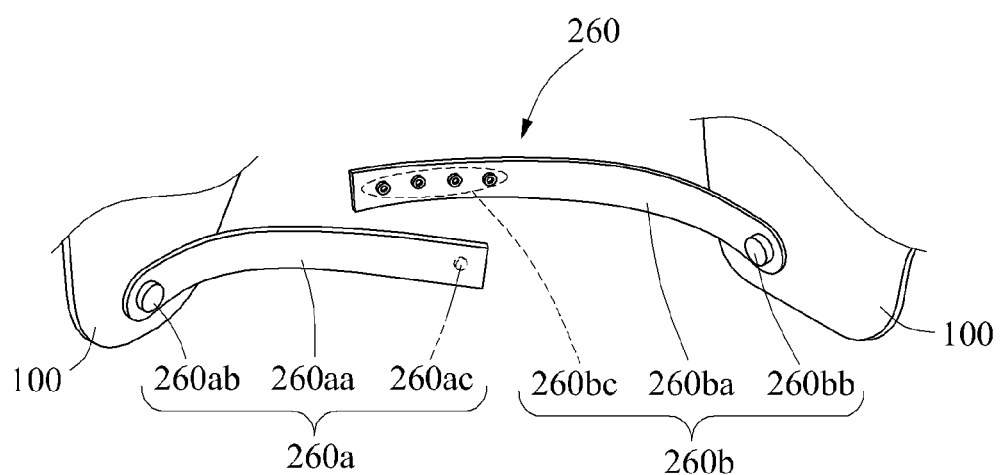
FIG. 7 is a view illustrating a modified example of a reinforcement belt according to at least one example embodiment.

FIG. 7 is a view illustrating a modified example of a reinforcement belt according to at least one example embodiment.

Referring to FIG. 7, a reinforcement belt 260 may include a first sub-belt 260*a* and a second sub-belt 260*b* that, in some example embodiments, may be detachable from each other in a manner of a snap fastener. For example, the sub-belt connecting portion 160*ac* may include a snap fastener. In other example embodiments, a length of the reinforcement belt 260 may be adjusted in a manner of a buckle. For example, the sub-belt connecting portion 160*ac* may include a buckle. However, the manner to adjust the length of the reinforcement belt 260 is not limited by the structures illustrated in FIGS. 6 and 7.

Figure 8:
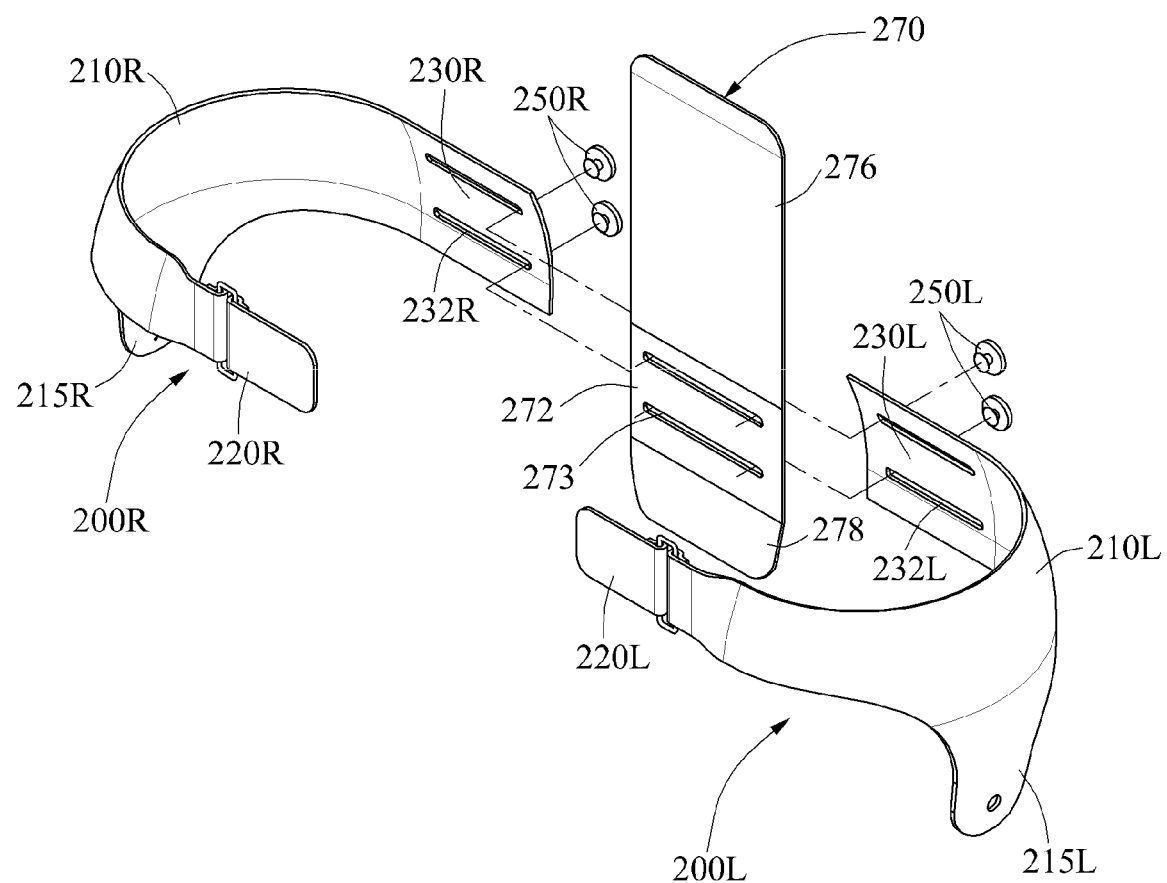
FIG. 8 is an exploded perspective view of a frame module according to at least one example embodiment.
Figure 9:
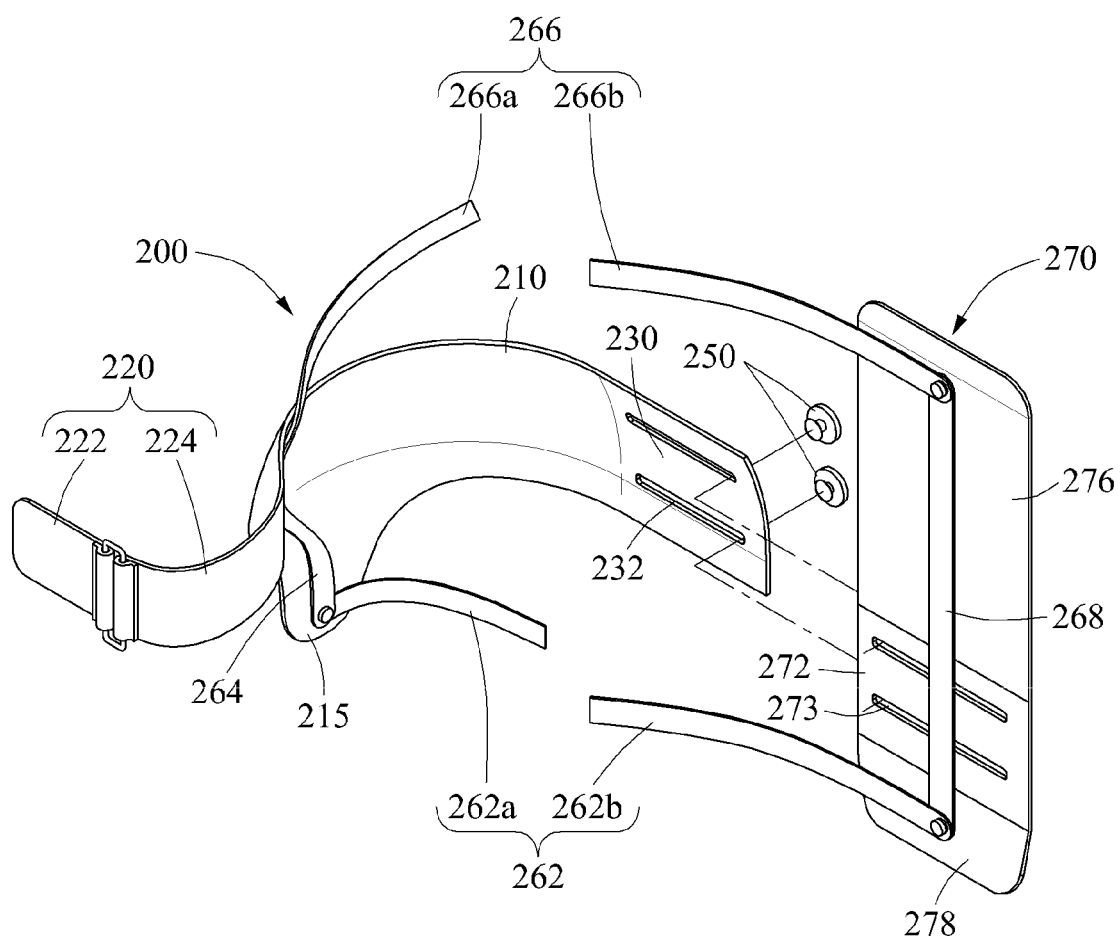
FIG. 9 is a view illustrating an installation structure of a reinforcement belt according to at least one example embodiment.

FIG. 8 is an exploded perspective view of a frame module according to at least one example embodiment, and FIG. 9 is a view illustrating an installation structure of a reinforcement belt according to at least one example embodiment.

Referring to FIGS. 8 and 9, a frame module 22 may include a first side frame 200L, a second side frame 200R, a fastening member 250, and a supporting member 270. The supporting member 270 may include a fixing portion 272, an upper supporting member 276, and a lower supporting member 278.

The fixing portion 272 may overlap the first side frame 200L and the second side frame 200R. A first rear extending portion 230L may be fixed to one side of the fixing portion 272, and a second rear extending portion 230R may be fixed to another side of the fixing portion 272. A third guide portion 273 may be provided in the fixing portion 272. The third guide portion 273 may be provided in a shape corresponding to a first guide portion 232L and a second guide portion 232R.

The upper supporting member 276 may extend from the fixing portion 272 in an upward direction to support an upper side of the user. The upper supporting member 276 may extend in a direction orthogonal to a longitudinal direction of the fixing portion 272. For example, the upper supporting member 276 may support a dorsal portion of the user. The upper supporting member 276 may extend from the fixing portion 272 to a portion corresponding to a midpoint of the dorsal portion of the user.

The lower supporting member 278 may extend from the fixing portion 272 in a downward direction to support a lower side of the user. The lower supporting member 278 may extend in a direction orthogonal to the longitudinal direction of the fixing portion 272. For example, the lower supporting member 278 may support a hip portion of the user.

The fastening member 250 may include a first fastening member 250L configured to fasten the first rear extending portion 230L with the fixing portion 272, and a second fastening member 250R configured to fasten the second rear extending portion 230R with the fixing portion 272. In other example embodiments, a single fastening member may be used to fasten the first rear extending portion 230L and the second rear extending portion 230R with the fixing portion 272.

The frame module 22 may include at least one of joint belts 262 and 264, supporting belts 262 and 268, crossing belts 264, 266, and 268, a parallel belt 262, a bone belt 264, a connecting belt 268, and a side belt 266.

Figure 10:
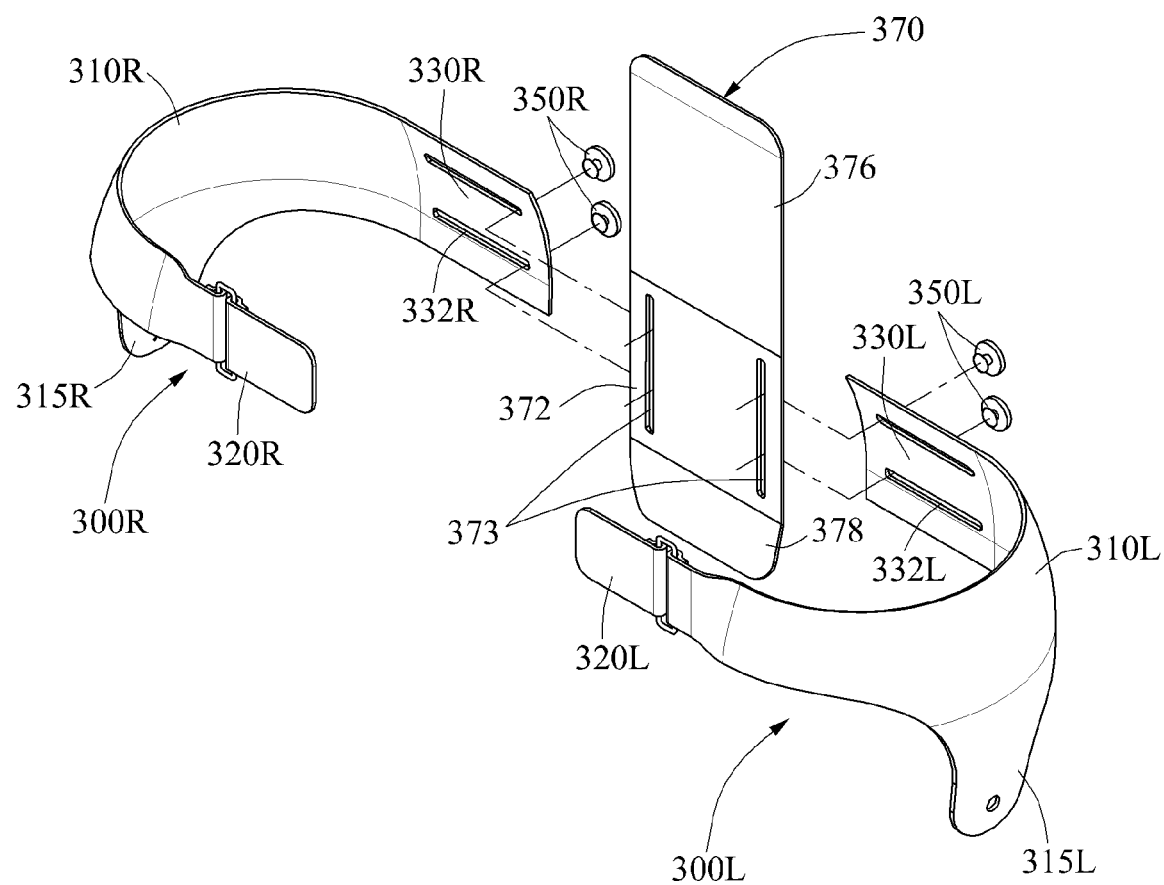
FIG. 10 is an exploded perspective view of a frame module according to at least one example embodiment.
Figure 11:
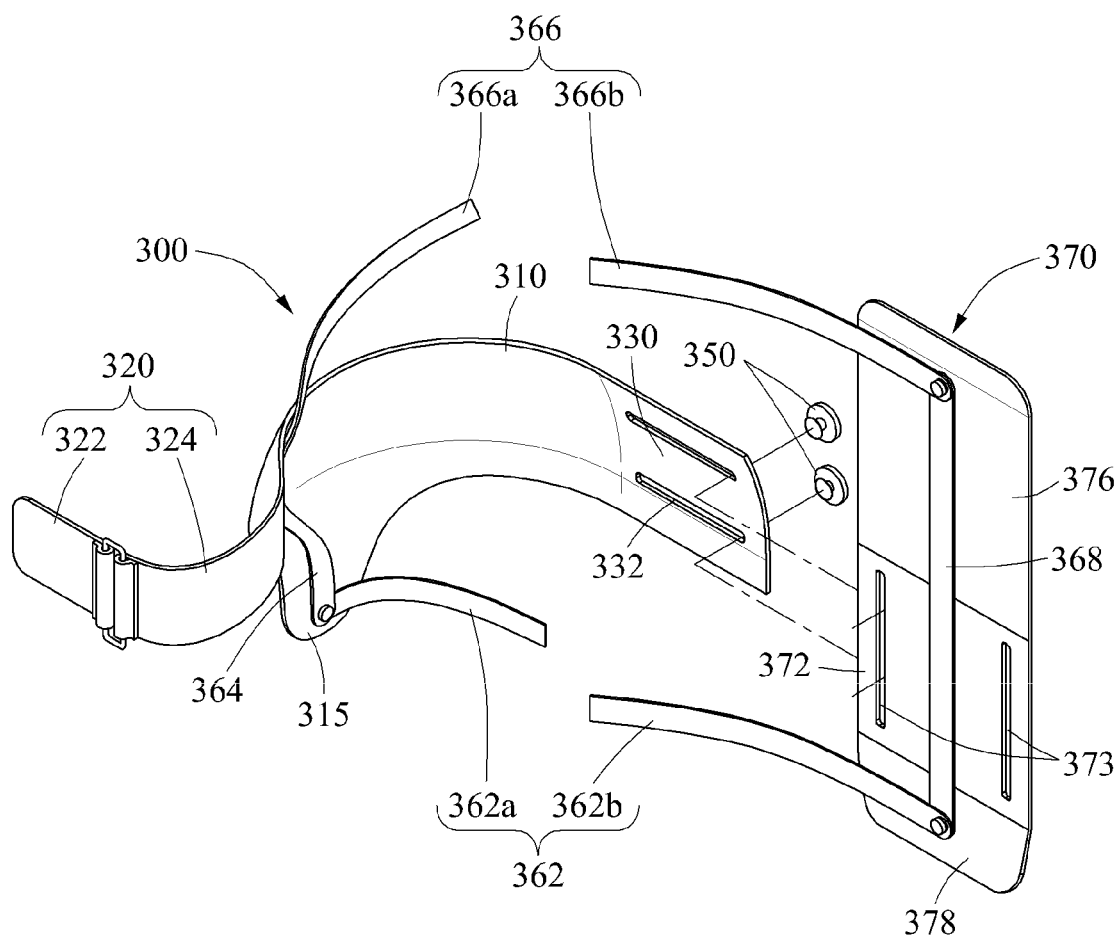
FIG. 11 is a view illustrating an installation structure of a reinforcement belt according to at least one example embodiment.

FIG. 10 is an exploded perspective view of a frame module according to at least one example embodiment, and FIG. 11 is a view illustrating an installation structure of a reinforcement belt according to at least one example embodiment.

Referring to FIGS. 10 and 11, a frame module 23 may include a first side frame 300L, a second side frame 300R, a fastening member 350, and a supporting member 370. The supporting member 370 may include a fixing portion 372, an upper supporting member 376, and a lower supporting member 378.

The fixing portion 372 may overlap the first side frame 300L and the second side frame 300R. A first rear extending portion 330L may be fixed to one side of the fixing portion 372, and a second rear extending portion 330R may be fixed to another side of the fixing portion 372. A third guide portion 373 may be provided in the fixing portion 372.

The third guide portion 373 may include a slot provided in a direction perpendicular to a first guide portion 332L of the first side frame 300L. The third guide portion 373 may further include a slot provided in a direction perpendicular to a second guide portion 332R of the second side frame 300R. By the third guide portion 373, a position of the supporting member 370 may be adjusted in a vertical direction with respect to the first side frame 300L or the second side frame 300R.

The fastening member 350 may include a first fastening member 350L configured to fasten the first rear extending portion 330L with the fixing portion 372, and a second fastening member 350R configured to fasten the second rear extending portion 330R with the fixing portion 372. In other example embodiments, a single fastening member may be used to fasten the first rear extending portion 330L and the second rear extending portion 330R with the fixing portion 372.

The frame module 23 may include at least one of joint belts 362 and 364, supporting belts 362 and 368, crossing belts 364, 366, and 368, a parallel belt 362, a bone belt 364, a connecting belt 368, and a side belt 366. The belts 362, 364, 366 and 368 may prevent an impact to the user caused in response to a distortion of a portion of the side frame 23 positioned at a relatively long distance from the driving module 30. In addition, the belts 362, 364, 366 and 368 may reduce an error or uncertainty caused in response to the distortion of the side frame 23, thereby helping to control assistance force precisely FIG. 12 is an exploded perspective view of a frame module according to at least one example embodiment, and FIG. 13 is a view illustrating an installation structure of a reinforcement belt according to at least one example embodiment.

Figure 12:
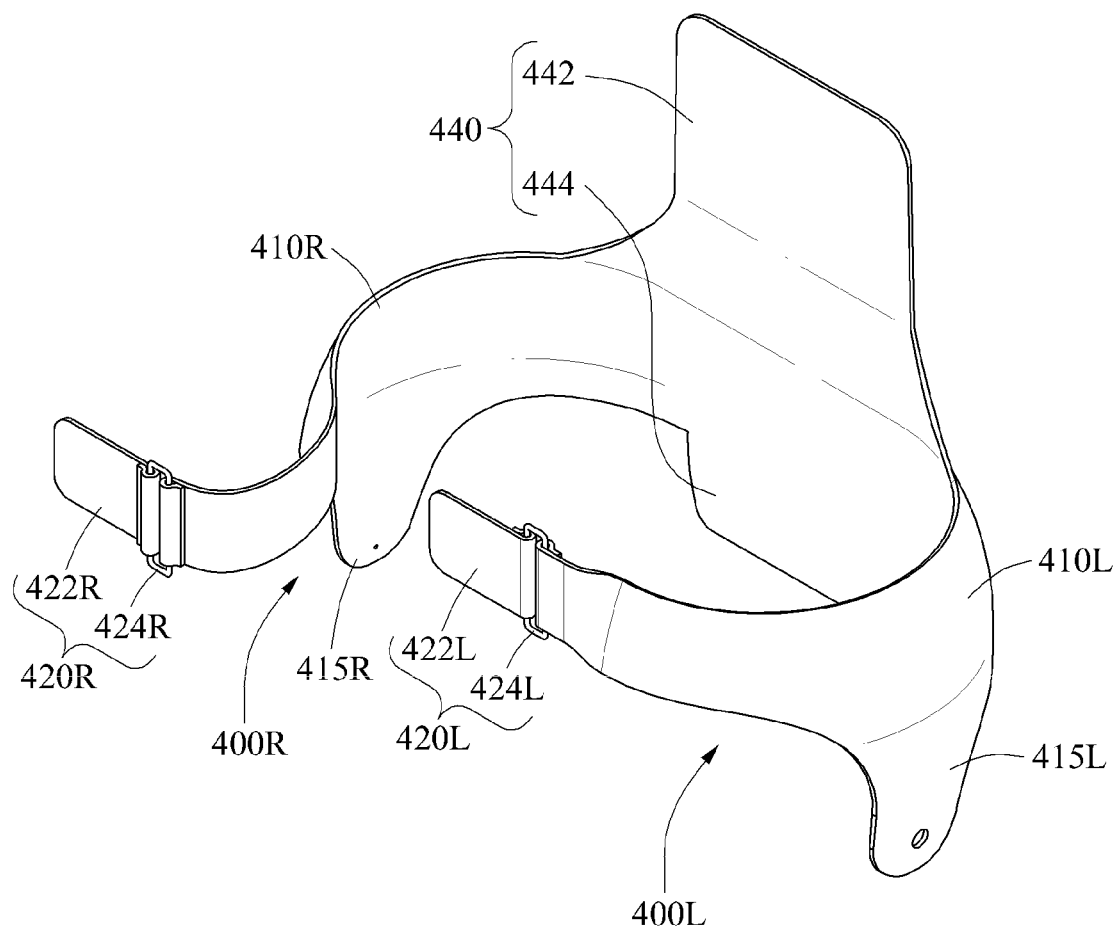
FIG. 12 is an exploded perspective view of a frame module according to at least one example embodiment.
Figure 13:
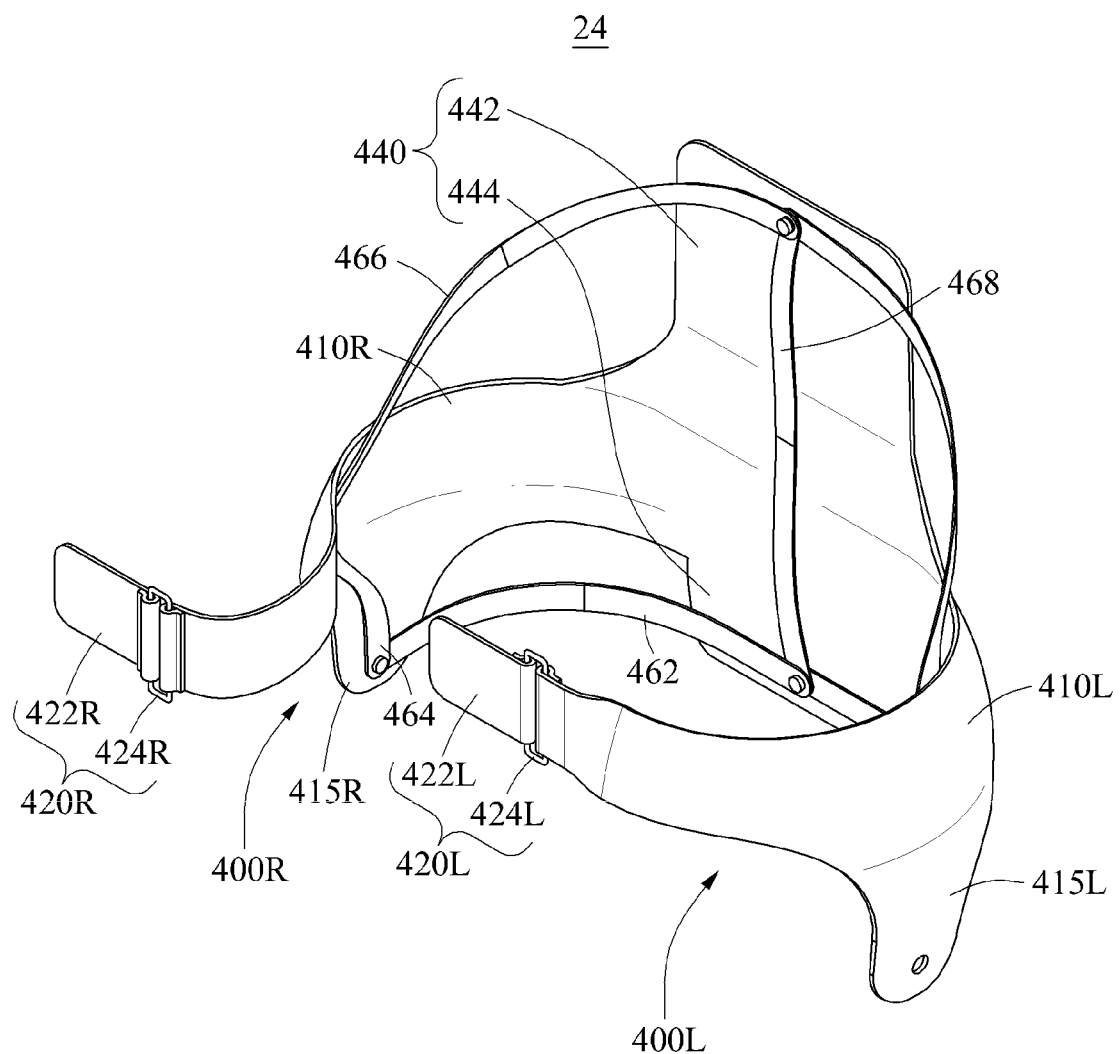
FIG. 13 is a view illustrating an installation structure of a reinforcement belt according to at least one example embodiment.

Referring to FIGS. 12 and 13, a frame module 24 may include a first side frame 400L, a second side frame 400R, and a supporting member 440. The supporting member 440 may include an upper supporting member 442, and a lower supporting member 444. Here, the first side frame 400L, the second side frame 400R, and the supporting member 440 may be provided as an integral body.

The frame module 24 may include at least one of joint belts 462 and 464, supporting belts 462 and 468, crossing belts 464, 466, and 468, a parallel belt 462, a bone belt 464, a connecting belt 468, and a side belt 466. The belts 462, 464, 466 and 468 may prevent an impact to the user caused in response to a distortion of a portion of the side frame 24 positioned at a relatively long distance from the driving module 30. In addition, the belts 462, 464, 466 and 468 may reduce an error or uncertainty caused in response to the distortion of the side frame 24, thereby helping to control assistance force precisely A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A motion assistance apparatus comprising:
    a driver configured to generate power to assist a motion of a user;
    a rotating member configured to be rotated using power received from the driver to assist a rotary motion of a leg and/or hip of the user; and
    a frame module including:
        a frame configured to at least partially enclose a portion of the user proximate a waist of the user, the frame including a rear portion corresponding to a first portion of the user proximate the waist of the user, a side portion corresponding to a second portion of the user proximate the waist of the user, and a front portion corresponding to a third portion of the user proximate the waist of the user, the side portion of the frame including a joint mounting portion configured to have the rotating member mounted thereto, the front portion including a first binding portion and a second binding portion, the second binding portion configured to detachably connect to the first binding portion; and
    at least one reinforcement belt, configured to be worn proximate the waist of the user, to reinforce a stiffness of the frame, the at least one reinforcement belt including at least a bone belt and a parallel belt for intersecting at the joint mounting portion and configured to directly connect the joint mounting portion of the side portion of the frame, the bone belt being arranged to incline upwardly from the joint mounting portion to the front portion and the parallel belt extending perpendicular to the bone belt and configured to sit about the third portion of the user.

2. The motion assistance apparatus of claim 1, wherein the at least one reinforcement belt is configured to have an adjustable length.

3. The motion assistance apparatus of claim 2, wherein the at least one reinforcement belt comprises:
    a first sub-belt having a first end portion and a second end portion, the first end portion of the first sub-belt connected to a first side of the frame; and
    a second sub-belt having a first end portion and a second end portion, the first end portion of the second sub-belt connected to a second side of the frame and the second end portion of the second sub-belt configured to detachably connect to the second end portion of the first sub-belt.

4. The motion assistance apparatus of claim 3, wherein the first end portion of at least one of the first sub-belt and the second sub-belt is rotatably connected to the frame.

5. The motion assistance apparatus of claim 1, wherein end portions of the at least one reinforcement belt are connected to inner surfaces of the frame such that the at least one reinforcement belt is configured to support the user in a state in which the user is spaced apart from the frame.

6. The motion assistance apparatus of claim 1, wherein at least one end portion of the reinforcement belt is rotatably connected to the frame.

7. The motion assistance apparatus of claim 1, wherein the at least one reinforcement belt includes a plurality of reinforcement belts connected to a single hinge axis associated with the frame.

8. The motion assistance apparatus of claim 1, wherein the at least one reinforcement belt includes a plurality of reinforcement belts connected together in a single closed loop.

9. The motion assistance apparatus of claim 1, wherein the frame further comprises:
    a supporting member configured to extend from the rear portion of the frame in a direction perpendicular to a circumferential direction of the portion of the user to support the user, and wherein
    the at least one reinforcement belt includes a supporting belt, the supporting belt having an end portion connected to an end portion of the supporting member.

10. The motion assistance apparatus of claim 1, wherein the frame includes,
    an upper supporting member configured to support the first portion of the user by extending upward from the rear portion of the frame vertically in a direction perpendicular to a circumferential direction of the portion of the user, and a lower supporting member configured to support the second portion of the user by extending downward in the direction perpendicular to the circumferential direction of the portion of the user, and wherein the at least one reinforcement belt further includes, an upper supporting belt having an end portion connected to the upper supporting member; and a lower supporting belt having an end portion connected to the lower supporting member.

11. The motion assistance apparatus of claim 1, wherein the at least one reinforcement belt further includes a crossing belt, the crossing belt connected to the frame in a direction intersecting a circumferential direction of the portion of the user.

12. The motion assistance apparatus of claim 1, wherein the parallel belt is connected to the frame in a direction parallel to a circumferential direction of the portion of the user.

13. The motion assistance apparatus of claim 12, wherein a first end of the parallel belt is configured to connect to the joint mounting portion, and the frame further comprises:

a supporting member configured to extend in a direction perpendicular to the circumferential direction of the portion of the user to support the user, a second end of the parallel belt configured to connect to the supporting member.

14. The motion assistance apparatus of claim 1, wherein the bone belt is configured to connect to the frame module in a longitudinal direction of an iliac crest of the user.

15. The motion assistance apparatus of claim 1, wherein the frame includes, an upper supporting member configured to support the first portion of the user by extending upward from the rear portion of the frame vertically in a direction perpendicular to a circumferential direction of the portion of the user, and a lower supporting member configured to support the second portion of the user by extending downward in the direction perpendicular to the circumferential direction of the portion of the user, and wherein the at least one reinforcement belt further includes a connecting belt configured to connect an end portion of the upper supporting member to an end portion of the lower supporting member.

16. The motion assistance apparatus of claim 1, wherein the frame includes a supporting member configured to extend in a direction perpendicular to a circumferential direction of the portion of the user to support the user, and the at least one reinforcement belt further includes a side belt having a first side and a second side, the first side of the side belt connected to the supporting member and the second side of the side belt connected to the front portion of the frame.

17. The motion assistance apparatus of claim 1, wherein the frame further comprises:

a supporting member configured to extend in a direction perpendicular to a circumferential direction of the portion of the user to support the user, and the at least one reinforcement belt includes a supporting belt having at least a first end portion connected to an end portion of the supporting member.

18. The motion assistance apparatus of claim 1, wherein the frame comprises:

a plurality of interlocking frames configured to enclose the portion of the user, and wherein the at least one reinforcement belt is configured to restrict deformation of the plurality of interlocking frames in response to a torque applied thereto.

19. The motion assistance apparatus of claim 18, wherein the plurality of interlocking frames are flexible frames and are separated by an adjustable distance to secure the frame module onto the portion of the user, the plurality of interlocking frames configured to have joint assemblies mounted thereon.

20. The motion assistance apparatus of claim 18, wherein the at least one reinforcement belt includes a plurality of reinforcement belts connected together in a closed loop.

* * * * *